United States Patent [19]

Roman et al.

[11] 4,020,061

[45] Apr. 26, 1977

[54] 3-OXOMETHYL-2-(1-NITRO-2-OXO-ETHYLIDENE)-TETRAHYDRO-2H-1,3-THIAZINES

[75] Inventors: Steven A. Roman, Oakdale, Calif.; James E. Powell, Rodmersham Green near Sittingbourne, England

[73] Assignee: Shell Oil Company, Houston, Tex.

[22] Filed: Mar. 3, 1976

[21] Appl. No.: 663,316

Related U.S. Application Data

[63] Continuation-in-part of Ser. No. 564,258, April 2, 1975, abandoned.

[52] U.S. Cl. .................. 260/243 R; 260/306.7 R; 260/294.8 D; 260/247.1 M; 424/246; 71/90

[51] Int. Cl.$^2$ .................................. C07D 279/06
[58] Field of Search ......................... 260/243 R

[56] References Cited

OTHER PUBLICATIONS

Hirai et al., *Chem. Pharm. Bull*, vol. 20, pp. 97–101 (1972).

*Primary Examiner*—John M. Ford

[57] ABSTRACT

Novel compounds defined in the title, useful as insecticides and herbicides.

1 Claim, No Drawings

3-OXOMETHYL-2-(1-NITRO-2-OXO-ETHYLIDENE)-TETRAHYDRO-2H-1,3-THIAZINES

This application is a continuation-in-part of copending application Ser. No. 564,258, filed Apr. 2, 1975, now abandoned.

DESCRIPTION OF THE INVENTION

It has been found that useful insecticidal and herbicidal activity is possessed by certain derivatives of 1,3-thiazacycloalkanes substituted at the 3-position (i.e., on the ring nitrogen atom) by an oxomethyl moiety, and at the 2-position by a 1-nitro-2-oxoethylidene moiety, these derivatives being described by the formula:

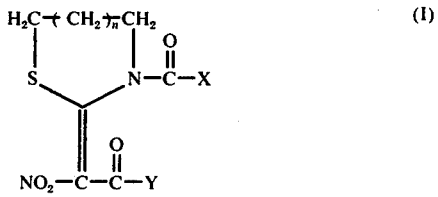

(I)

wherein $n$ is zero or one, X and Y each is R, R—O— or R—S—, containing up to 30 carbon atoms and being alkyl, alkenyl, alkynyl, cycloalkyl, cycloalkylalkyl, haloalkyl, haloalkenyl, mono- and poly(alkoxy)alkyl, alkylthioalkyl, alkylsulfinylalkyl, alkylsulfonylalkyl; 2,4-dichlorophenoxymethyl, 2-methyl-4-chlorophenoxymethyl, 2,4,5-trichlorophenoxymethyl; phenyl or phenalkyl, or either of these substituted on the ring by one to two of one or more of halogen, nitro, cyano, alkyl, aryl, alkoxy or phenoxy; is aminoalkyl, $(CH_2)_m NR^1R^2$, wherein $m$ is 1 or 2, $R^1$ and $R^2$ each is alkyl, alkenyl, cycloalkyl, phenyl or phenalkyl; or is $(CH_2)_n R^5$, wherein $n$ is zero, 1 or 2, and $R^5$ is heterocyclic moiety selected from furanyl, tetrahydrofuranyl, dioxolanyl, thienyl, thiopyranyl, pyridinyl, pyrrolidinyl, morpholinyl and their -methyl and -ethyl counterparts, with the proviso that one or both of X and Y is 2,4-dichloro-, 2-methyl-4-chloro- or 2,4,5-trichloro-phenoxymethyl.

When aliphatic, the moiety represented by R may be of straight-chain or branched-chain configuration and preferably contains no more than ten carbon atoms. The preferred aminoalkyl moieties are dialkylaminomethyl and -ethyl. The preferred phenyl moieties are optionally-substituted-phenyl. The preferred halophenoxymethyl moiety is 2,4-dichlorophenoxymethyl.

Because of their insecticidal and herbicidal activity characteristics, two preferred sub-classes of the genus of the invention consist of these compounds wherein $n$ is 1 and (a) Y is alkyl, or alkoxy, straight-chain or branched-chain in configuration, containing from one to six carbon atoms and X is 2,4-dichlorophenoxymethyl, and (b) Y is 2,4-dichlorophenoxymethyl and X is alkyl, or alkoxy, straight-chain or branched-chain in configuration, containing from one to six carbon atoms.

Compounds of this invention can be prepared by four general procedures, all involving treatment of an alkali metal (e.g., sodium) derivative of an appropriate thiazine precursor with the appropriate acid chloride, chloroformate or chlorothioformate, the four types of compounds involved being as follows:

A. X and Y both are RO— or RS—;
B. X is R and Y is RO— or RS—;
C. X and Y both are R;
D. X is RO— or RS— and Y is R.

The appropriate thiazine precursors are represented by the formulae:

1. For preparation of types A and B:

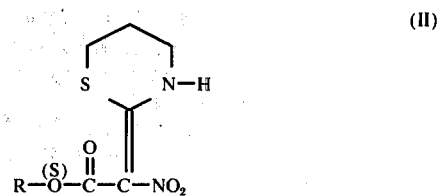

(II)

2. For preparation of types C and D:

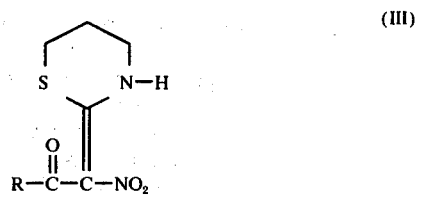

(III)

Compounds of formula II are the subject of application Ser. No. 554,371, now U.S. Pat. No. 3,962,234, while compounds of formula III are the subject of application Ser. No. 547,417 now U.S. Pat. No. 3,962,225. For the purpose of describing the preparation of these precursors, the pertinent portions of said applications are incorporated herein.

The acid chloride, chloroformate and chlorothioformate reactants are in many cases known compounds, and in those cases when they are specifically novel, can be prepared by the procedures known in the art for the known analogs thereof.

The thiazine precursors are converted to the needed alkali metal derivatives by treatment with an alkali metal hydride, such as sodium hydride, preferably in a suitable liquid reaction medium, such as tetrahydrofuran, at a low temperature, for example, about 0° C. To enable efficient control of the often exothermic reaction, it may be found desirable to add slowly a solution or suspension of the thiazine to a stirred, cooled solution or suspension of the base, the mixture being stirred further until hydrogen ceases to evolve. The mixture then may be allowed to warm, for example to room temperature, to ensure completion of the reaction.

Treatment of the alkali metal derivative with the carbonylic reactant can be effectively carried out under similar conditions: adding a suspension or solution of the carbonylic reactant slowly to a stirred solution or suspension of the alkali metal derivative, the reaction mixture being cooled as necessary to maintain it at a low temperature — again, suitably about 0° C — then allowing the stirred mixture to warm, for example to room temperature, and stirring the warmed mixture for a period of time to ensure complete reaction.

It often will be found convenient to employ the same liquid reaction medium in both steps of the process, with tetrahydrofuran generally being quite suitable for this purpose. In such a case, the solution or suspension of the alkali metal derivative obtained as the product of the alkali metal hydride/thiazine reaction is treated directly with the solution or suspension of the carbonylic reactant.

The desired product can be isolated from the crude reaction mixture and purified by conventional methods, such as filtration, extraction, crystallization and elution (chromatography).

Preparation of compounds of type A also can be effected by treating a precursor of formula II with the appropriate acid anhydride, in a suitable solvent, such as methylene chloride or other haloalkane, using reaction conditions and product recovery and purification techniques described above.

As is disclosed in application Ser. No. 554,371, now U.S. Pat. No. 3,962,234 precursors of type B also can be prepared by treating tetrahydro-(2-nitromethylene)-2H-1,3-thiazine with a 1-(R-oxycarbonyl)-3-methylimidazolium chloride by the method described by E. Guibe-Jampel, et al., Bull. Soc. Chim. Fr. 1973 (3) (Pt. 2), pp. 1021–7. According to this method, the imidazolium chloride is prepared by treating 1-methylimidazole with the appropriate chloroformate, R—O—C(O)—Cl, preferably in a suitable solvent and at a low temperature, for example, about 0° C. A suitable general method for conducting this procedure comprises adding a solution of the chloroformate in a tetrahydrofuran slowly (e.g., dropwise) to a cold (e.g., 0°) solution of the N-methylimidazole in the same solvent, stirring the cold mixture for a period of from about 15 minutes to 1 hour to ensure complete reaction, then adding to that stirred cold mixture a solution of the thiazine, then warming the stirred mixture to a temperature of from about room temperature to the reflux temperature, and stirring the warm mixture for a time to ensure complete reaction.

The desired product can be isolated from the crude reaction mixture and purified by conventional methods, such as filtration, extraction, crystallization and elution (chromatography).

These procedures for preparing compounds of this invention are illustrated in the following examples of the preparation of particular species of such compounds. In all cases the identity of the precursor had been established and the identity of the final product was confirmed, by elemental analysis and by infrared and nuclear magnetic resonance spectrum analyses:

EXAMPLE 1 methyl (3-((2,4-dichlorophenoxy)-acetyl)tetrahydro-2H-1,3-thiazin-2-ylidene)nitroacetate (1)

To a mixture of 221 g of 5,6-dihydro-2-(methylthio)-4H-1,3-thiazine (A. F. McKay et al., J. Am. Chem. Soc., 80, 3339 (1950)) and 1 g of zinc chloride at about 100°, 202 g of methyl nitroacetate (S. Zen et al., Kogyo Kagaku Zosshi, 74, 70 (1971)) was added dropwise over a 30-minute period. The resulting mixture was heated for 4 hours at 95°–105° C. 200 ml of isopropyl alcohol then was added to the hot mixture, then 400 ml of ether was added. The resulting mixture was filtered to give methyl nitro (tetrahydro-2H-1,3-thiazin-2-ylidene)acetate (1A), as a pale yellow solid, m.p.: 107°–108°.

6.6 g of 1A was added slowly to 1.5 g of sodium hydride in 100 ml of tetrahydrofuran at 5°–10°. When gassing ceased, the mixture was warmed to room temperature and stirred for 1 hour. It then was cooled to 5°, and a solution of 7.9 g of 2,4-dichlorophenoxyacetyl chloride in 30 ml of tetrahydrofuran was added. The mixture then was allowed to warm to room temperature and stirred overnight. The mixture then was poured into 1 liter of water and extracted with 1 liter of ether. The separated ether phase was washed with water, dried (MgSO$_4$) and filtered, and the ether was evaporated to give a yellow oil. The oil was passed through Florisil, using methylene chloride as eluent. The solvent was evaporated and the solid taken up in ethanol, from which a solid was separated. The ethanol was evaporated to give an oil, which was stripped under vacuum. The residue was triturated with ether to give 1, as a yellow solid, m.p.: 133° (with decomposition).

EXAMPLES 2–4

By a procedure analogous to that described in Example 1, the following additional individual species of compounds of formula I were prepared, each compound being described in terms of (a) example number, (b) compound number, (c) definitions of the moieties defined by X and Y and (d) physical description.

2; 2; 2,4-dichlorophenoxymethyl; ethoxy; orange oil, boiling point not determined;

3; 3; 2,4-dichlorophenoxymethyl; isopropoxy; yellow oil, boiling point not determined;

4; 4; 2,4-dichlorophenoxymethyl; phenoxy; yellow oil, boiling point not determined;

EXAMPLE 5

1-(3-acetyltetrahydro-2H-1,3-thiazin-2-ylidene)-3-(2,4-dichlorophenoxy)-1-nitro-2-propanone (5)

To a mixture of 235 g of 5,6-dihydro-2-(methylthio)-4H-1,3-thiazine (A. F. McKay et al., J. Am. Chem. Soc., 80, 3339 (1950)) and 2g of zinc chloride at approximately 115° in a nitrogen atmosphere, 263 g of ethyl nitroacetate (S. Zen et al., Kogyo Kagaku Zosshi, 74, 70 (1971)) was added dropwise over a 1.5 hour period. The mixture was held at 110°–120°. When evolution of methyl mercaptan ceased after 45 minutes further stirring of the heated mixture, 1 g of zinc chloride was added and the mixture was stirred at about 115° for 1.25 hours. An additional 1 g of zinc chloride then was added and stirring of the mixture at about 115° was continued for 1.5 hours. The mixture then was poured into a cooled 2/1 ether/isopropyl alcohol mixture. The crystallized product was collected, washed with ether and dried under reduced pressure to leave a tan solid, m.p. 100°–102°, which on recrystallization from methanol gave ethyl nitro(tetrahydro-2H-1,3-thiazin-2-ylidene)acetate (5A), as a pale yellow solid, m.p. 105°–106°.

2.3 g of 5A was added to 10 ml of 20% aqueous sodium hydroxide and the mixture was stirred at room temperature for 12 hours. The resulting solution was treated dropwise with 3.5 g of acetic acid. The addition was accompanied by vigorous gas evolution. The resulting mixture was extracted with methylene chloride and the extract was dried (magnesium sulfate) and concentrated under reduced pressure to give tetrahydro-2-(nitromethylene)-2H-1,3-thiazine (5B) as a pale yellow solid, m.p. 76°–78°.

A solution of 7.2 g of 2,4-dichlorophenoxyacetyl chloride in 20 ml of tetrahydrofuran was added dropwise to a solution of 2.5 g of 1-methylimidazole in 80 ml of tetrahydrofuran at 0.5°. The resulting slurry was stirred for 30 minutes at 5°, then 4.8 g of 5B was added all at once. The mixture was stirred overnight. Then 0.5 equivalent mole of the imidazole complex in 50 ml of tetrahydrofuran was prepared and added at 5°. The stirred mixture was allowed to rise slowly to room temperature, and stirred overnight. The solvent was stripped; the residue was treated with 1:1 volume mixture of water and methylene chloride. The phases were separated, the water phase was extracted with methylene chloride, the methylene chloride solutions were combined, washed with water and saturated salt solution, dried (MgSO$_4$) and the solvent was stripped to give an oil. The oil was passed through Florisil to give a mush, which was triturated with pentane to give 3-(2,4-dichlorophenoxy)-1-nitro-1-(tetrahydro-2H-1,3-thiazin-2-ylidene)-2-propanone (5C), as a pale yellow solid, m.p.: 164°–164.5°.

5 was prepared as a yellow solid, melting point: 120°–120.5° (with decomposition) by the treatment of 5C with sodium hydride and acetyl chloride, by the general procedure described in Example 1.

EXAMPLES 6 AND 7

By analogous procedures, using 5C as precursor, the following additional individual species of the compounds of Formula I were prepared, the mode of identification being that employed in Examples 2–4.

6; 6; phenyl; 2,4-dichlorophenoxy; yellow solid, m.p.; 143° (with decomposition);

7; 7; methoxy; 2,4-dichlorophenoxy; yellow oil, boiling point not determined.

EXAMPLE 8 ethyl (3-((2,4-dichlorophenoxy)acetyl)-2-thiazolidinylidene)nitroacetate (8)

8 was prepared as a yellow solid, m.p.: 138° (with decomposition) from ethyl nitro-2-thiazolidinylideneacetate (K. Hirai et al., Chem. Pharm. Bull. (Japan), 20(1) 97–101 (1972)) by the procedure described in Example 1.

The compounds of this invention exhibit useful herbicidal activity, particularly for post-emergent application for the control of broad-leaved weeds. Additionally, the compounds of the invention wherein n is 1 have shown moderate to high activity with respect to *Heliothis zea* (corn earworm, cotton bollworm, tomato fruitworm).

The pre-emergence herbicidal activity of compounds of this invention was evaluated by planting seeds of barnyard grass, garden cress, downy brome, wild mustard, green foxtail, velvet leaf, soybean, grain sorghum, cotton and wheat in soil treated with test compound at a set dosage. The planted soil was held under controlled conditions of temperature, moisture, and light for 13 to 14 days. The amount of germination was then noted and the effectiveness of the test compound was rated visually, on the basis of a 0 to 9 scale, 0 rating indicating no effect, 9 indicating death of the seedlings or no germination.

The post-emergence activity of compounds of this invention was evaluated by spraying 7-day old crabgrass plants, 10-day old pigweed plants, 7-day old downy brome plants, 10-day old wild mustard, 10-day old green foxtail, 10-day old grain sorghum, 14-day old cotton plants and 7-day old wheat plants to runoff with a liquid formulation of the test compound at two set dosages. The sprayed plants were held under controlled conditions for 10 to 11 days and the effect of the test compound was then evaluated visually, the results being rated on the 0 to 9 scale described above.

The herbicidal activity of compounds of this invention was further determined with respect to several common species of weeds, by spraying a formulation of the test compound on to the soil in which the weed seeds had been planted (pre-emergence test) or on the foliage of growing plants (post-emergence test). In each series of tests the soil was held in containers that isolated that soil into a narrow band, or row. The solution of test compound was sprayed over the band, from one end to the other, the concentration of the test compound in the formulation varying logarithmically from a higher value at one end of the band to a lower value at the other end of the band. The effect of the test compound was evaluated visually and reported as the nominal rate of application, in pounds of test compound per acre of the soil band, at which 90% inhibition of the growth of the weeds occurred.

The compounds of the invention were found to have an activity pattern similar to that of 2,4-dichlorophenoxyacetic acid and related compounds, being primarily of interest for post-emergence selective control of broad-leaved weeds.

When applied as herbicide, a compound of the invention ordinarily is formulated with a carrier and/or a surface active agent.

By "carrier" is meant here a solid or fluid material, which may be inorganic or organic and of synthetic or natural origin, with which the herbicide is mixed or formulated to facilitate its application to the plant, seed, soil or other object to be treated, or its storage, transport or handling.

The surface-active agent may be an emulsifying agent or a dispersing agent or a wetting agent; it may be nonionic or ionic.

Any of the carrier materials or surface-active agents usually applied in formulating pesticides may be used, and suitable examples of these are to be found, for example, in U.K. Patent specification No. 1,232,930.

The compositions may be formulated as wettable powders, dusts, granules, solutions, emulsifiable concentrates, emulsions, suspension concentrates to contain 25, 50 or 75%w of toxicant and usually contain, in addition to solid carrier, 3–10%w of a dispersing agent and, where necessary, 0–10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of toxicant. Granules are usually prepared to have a size between 10 and 100 BS mesh (1.676–0.152 mm), and may be manufactured by agglomeration or impregnation techniques. Generally, granules will contain ½–25%w active ingredient and 0–10% w of additives such as stabilizers, slow release modifiers and binding agents. Emulsifiable concentrates usually contain, in addition to the solvent and, when necessary, co-solvent, 10–50%w/v active ingredient, 2–20%w/v emulsifiers and 0–20%w/v of appropriate additives such as stabilizers, penetrants and corrosion inhibitors. Suspension concentrates are compounded so as to obtain a stable non-sedimenting, flowable product and usually contain 10–75%w active ingredient, 0.5–15%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the active ingredient is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate with water, also are contemplated. The emulsions may be of the water-in-oil or of the oil-in-water type, and may have a thick "mayonnaise"-like consistency.

The compositions may also contain other ingredients, for example, other compounds possessing pesticidal, especially insecticidal, acaricidal, herbicidal or fungicidal properties.

The amount of the herbicide of this invention necessary to kill or inhibit the growth of plants is defined as the herbicidal amount. When the compounds are used as pre-emergence herbicides, an application rate of about 0.5 to about 20 pounds per acre is used, with about 1 to about 10 pounds per acre being preferred. When the compounds are used as post-emergence herbicides, an application rate of about 0.01 to about 20 pounds per acre of one or more active compounds per acre is used, with an application rate of about 0.1 to about 3 pounds per acre being preferred. This quantity will obviously vary with the individual species of herbicide, the plant species, type of formulation, environmental conditions and the like. Those versed in the herbicide field, can readily determine the effective amount for a particular set of condition.

Activity of compounds of this invention with respect to insects was determined by using standardized tests to establish the $LC_{50}$ dosage (in milligrams of test compound per 100 milliliters of solvent or liquid carrier required in the solution or suspension of test compound used) that was required to kill 50% of the test insects. The test insects were the housefly, corn earworm, mosquito, pea aphid and 2-spotted spider mite.

Compound 7 was found to have low toxicity to the housefly; otherwise, none of the compounds was found to have more than slight activity to the mites, aphids, houseflies and mosquito larva. Compounds 1, 3, 5, 6, and 7 were found to have moderate activity to the corn earworm, compounds 2 and 4 being quite active, and compound 8 being inactive.

When applied as an insecticide, a compound of the invention ordinarily is formulated with an adjuvant — that is, a carrier optionally a surface-active agent.

The term "carrier" in this regard means a material which may be inorganic or organic and of synthetic or natural origin with which the insecticide is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as for example, coumarone resins, polyvinyl chloride and styrene polymers and copolymers, solid polychlorophenols; bitumen, waxes such as beeswax, paraffin wax and chlorinated mineral waxes; degradable organic solids such as ground corn cobs and walnut shells; and solid fertilizers, for example, superphosphates.

Suitable liquid carriers include solvents for the compounds of this invention and liquids in which the toxicant is insoluble or only slightly soluble.

Examples of such solvents and liquid carriers generally are water, alcohols, for example, isopropyl alcohol, ketones, such as acetone, methyl ethyl ketone, methyl isobutyl ketone and cyclohexanone; ethers; aromatic hydrocarbons, such as benzene, toluene and xylene; petroleum fractions, such as kerosene, light mineral oils, chlorinated hydrocarbons, such as carbon tetrachloride, perchlorethylene, trichloroethane, including liquefied normally vaporous gaseous compounds. Mixtures of different liquids are often suitable.

If used, the surface-active agent may be an emulsifying agent of a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earch metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated caster oil, and sodium alkaryl sulfonates such as sodium dodecylbenzene sulfonate; and polymers of ethylene oxide and copolymers of ethylene oxide and propylene oxide.

The compositions may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3–10%w of stabilizer(s) and/or other additives such as penetrants or stickers. Dusts are usually formulated as a dust concentrate having a similar compositions to that of a wettable powder but without a dispersant, and are diluted in the field with further solid carrier to give a composition usually containing ½–10%w of toxicant. Granules may be manufactured by agglomeration or impregnation techniques. Generally, granules will contain ½–25%w toxicant and 0–10%w of additives such as stabilizers, slow release modifiers and binding agents. Emulsifiable concentrates usually contain, in addition to the solvent, and when necessary, co-solvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in prevent sedimentation or as antifreeze agents for water.

Aqueous dispersions and emulsions, for example, compositions obtained by diluting a wettable powder or an emulsifiable concentrate with water, also are contemplated.

The compositions may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of insecticide at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosagee of active material at the locus being within the skill of those versed in the art. In general, however, the effective dosage of insecticides of this invention at the locus to be protected — i.e. the dosage to which the insect contacts — is of the order of 0.001% to 0.5% based on the total weight of the formulations, though under some circumstances the effective concentration will be as little as 0.0001% or as much as 2%, on the same basis.

We claim as our invention:

1. A compound of the formula:

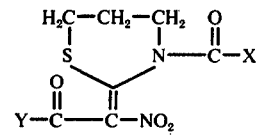

wherein X and Y each is R, R—O— or R—S—, R containing up to 30 carbon atoms and being alkyl, alkenyl, alkynyl, cycloalkyl, cycloalkylalkyl, haloalkyl, haloalkenyl, mono- and poly(alkoxy)alkyl, alkylthioalkyl, alkylsulfinylalkyl, alkylsulfonylalkyl; 2,4-dichlorophenoxymethyl, 2-methyl-4-chlorophenoxymethyl, 2,4,5-trichlorophenoxy-methyl; phenyl or phenalkyl, or any of these substituted on the ring by one to two of one or more of halogen, nitro, cyano, alkyl, phenyl, alkoxy or phenoxy; is aminoalkyl, $-(CH_2)_m NR^1R^2$, wherein $m$ is 1 or 2, $R^1$ and $R^2$ is alkyl, alkenyl, cycloalkyl, phenyl or phenalkyl; or is $-(CH_2)_n R^5$, wherein $n$ is zero, 1 or 2, and $R^5$ is heterocyclic moiety selected from furanyl, tetrahydrofuranyl, dioxolanyl, thienyl, thiopyranyl, pyridinyl, pyrrolidinyl, morpholinyl and their -methyl and -ethyl counterparts, with the proviso that one or both of X and Y is 2,4-dichloro-, 2-methyl-4-chloro- or 2,4,5-trichloro-phenoxymethyl.

* * * * *